United States Patent [19]

Sapia

[11] Patent Number: 4,942,545
[45] Date of Patent: Jul. 17, 1990

[54] CALIBRATION OF EDDY CURRENT PROFILOMETRY

[75] Inventor: Mark A. Sapia, Canton, Conn.

[73] Assignee: Combustion Engineering, Inc., Windsor, Conn.

[21] Appl. No.: 202,503

[22] Filed: Jun. 6, 1988

[51] Int. Cl.⁵ .......................... G01B 7/00; G06F 11/00
[52] U.S. Cl. ............................. 364/571.01; 364/560; 33/504; 73/1 J; 324/228
[58] Field of Search ................ 364/571.01, 571.02, 364/571.07, 560–564; 33/1 V, 1 BB, 502, 504, 505, 529, 702, 833, 501.6; 324/207, 208, 221, 228, 229; 73/1 R, 1 J, 105

[56] References Cited

U.S. PATENT DOCUMENTS

| | | | |
|---|---|---|---|
| 3,356,938 | 12/1967 | Wood | 324/221 |
| 3,940,689 | 2/1976 | Johnson, Jr. | 324/221 |
| 4,292,589 | 9/1981 | Bonner | 324/221 |
| 4,320,340 | 3/1982 | Lichtenberg | 324/221 |
| 4,611,304 | 9/1986 | Butenko et al. | 364/571.07 |
| 4,750,141 | 6/1988 | Judell et al. | 364/571.01 |
| 4,751,461 | 6/1988 | McWhirter et al. | 324/221 |
| 4,766,374 | 8/1988 | Glass, III et al. | 324/207 |
| 4,771,237 | 9/1988 | Daley | 73/1 J |

Primary Examiner—Parshotam S. Lall
Assistant Examiner—Joseph L. Dixon
Attorney, Agent, or Firm—Chilton, Alix & Van Kirk

[57] ABSTRACT

Calibration of an eddy current probe (24) and associated data acquisition and analysis system (42, 48, 52, 54, 66) is accomplished using a step tube sample (68) having a nominal diameter portion (74) substantially equivalent to a nominal field tube (22). Two readings of eddy current test units are obtained from the step tube sample, and the diameter of the probe is used as a boundary condition on the non-linear response of the probe to variations in tube radius. A calibration curve is generated for use in converting field tube eddy current measurements to field tube radius or profile.

6 Claims, 5 Drawing Sheets

CALIBRATION OF EDDY CURRENT PROFILOMETRY

BACKGROUND OF THE INVENTION

The present invention relates to nondestructive testing techniques, and more particularly to the calibration of eddy current testing equipment for measuring the profile of a tube or the like.

In numerous industrial installations, and particularly nuclear power plants, a variety of different types of tubes are configured for the purpose of carrying steam or process fluid, or for serving as a sheath or sleeve for guiding the movement of a rod. Due to mechanical, thermal, or other stresses, such tubes may experience slight deformation which, if not identified quickly, can lead to significant bending and adversely affect the performance of the tube and even the entire industrial process.

Conventionally, eddy current inspection techniques have been used to assess the degree to which the circularity of a tube cross section has deteriorated. Typically, an eddy current probe is advanced through the tube at a known rate, and data are collected from for example, eight eddy current sensors surrounding the probe. The resulting data must then be analyzed to determine tube circularity as a function of axial location along the tube.

Equipment of this type includes the Zetec MIZ-18 System, available from the Zetec Company. The Zetec and similar equipment must be properly calibrated in order for the acquired data to provide accurate results regarding the tube profile. The probe output signal is typically non-linear with respect to changes in the tube radius. Conventionally, a step tube is used as a calibration standard associated with a particular inspection application. For example, if the tubes of a nuclear steam generator are to be inspected, the material, nominal ID of the tubes and probe body diameter dictate the type of step tube used for calibration. For a steam generator tube of Inconnel material with a nominal ID of 0.654 inch, a step tube of the same material has two regions, one with an ID of 0.654 inch and another with an ID of, for example 0.577 inch.

The equipment operator obtains probe output readings (hereinafter referred to as eddy current test units, or "ECTU") for the nominal and step regions of the step tube standard. These inspection data are acquired from the steam generator tubes, as a function of probe axial position in the tubes. Conventionally, the step tube readings are used to look up tabular calibration correction values for the ECTU of the steam generator tubes. This look up can be manual, or the "look up table" can be in the form of a data base in the memory of a computer.

SUMMARY OF THE INVENTION

It is an object of the present invention, to improve and simplify the calibration associated with the reduction of ECTU data acquired during the course of inspecting a tube profile.

It is a more particular object of the invention, to improve and simplify the calibration associated with the use of a two-region step tube standard during the course of inspecting a tube profile.

This object is accomplished in accordance with a system and method by which two ECTU readings obtained from the step tube sample, are used to obtain an explicit, non-linear calibration curve, relating ECTU to tube internal radius. The calibration curve simplifies the determination of the profiles of the inspected tubes.

BRIEF DESCRIPTION OF THE DRAWINGS

These and other objects and advantages are accomplished with the preferred embodiment of the invention as described below with reference to the accompanying drawings, in which.

DESCRIPTION OF THE PREFERRED EMBODIMENT

Figure 1:
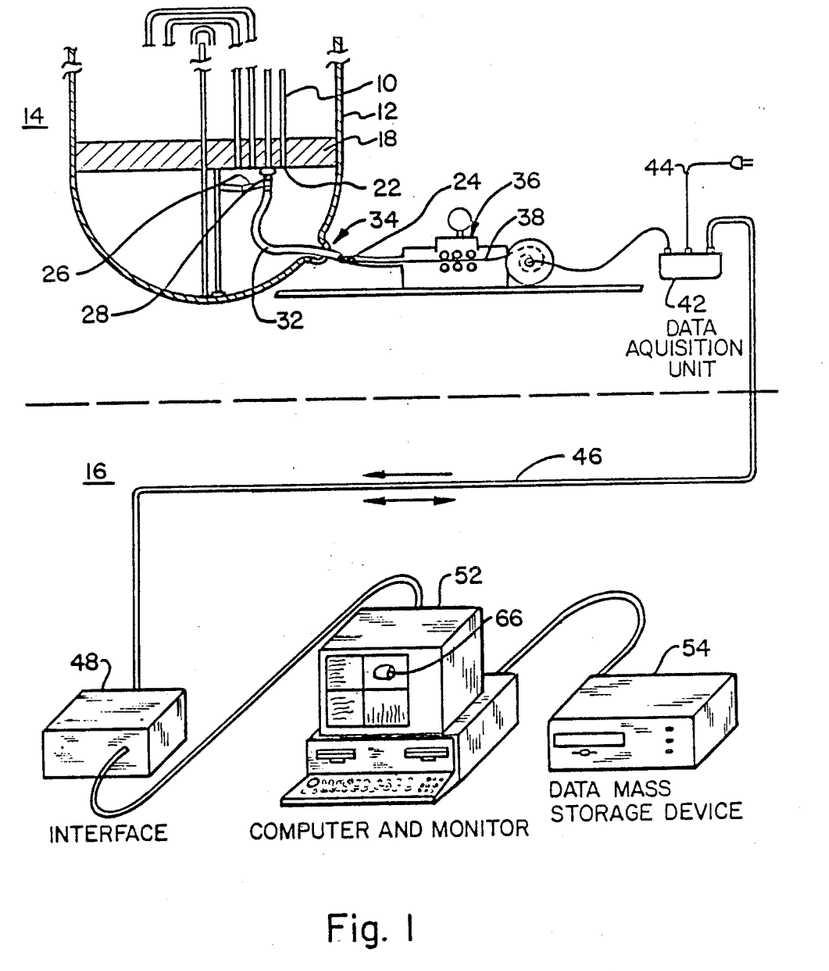
FIG. 1 is a schematic representation of an array of steam generator tubes and an eddy current probe system for non-destructively inspecting the tube profiles as a function of axial position along the tube.

FIG. 1 shows a system for the eddy current inspection of the internal profile of each of a plurality of tubes 10 in a nuclear steam generator 12. Although the description of the preferred embodiment will be directed to the inspection of steam generator tubes, it should be appreciated that other tubes having a nominal, cylindrical diameter could also be inspected with apparatus and method according to the present invention.

FIG. 1 is schematically divided into two portions 14 and 16, the upper representing the interior of the containment building of a nuclear power plant, in the vicinity of the steam generator 12, and the lower portion representing equipment typically located in a data acquisition trailer (not shown), situated outside the containment building.

In a typical steam generator 12, a tube sheet 18 supports the open lower ends 22 of a plurality of vertically extending U-tubes, through which an eddy current inspection probe 24 is to be passed. Typically, fixture equipment, such as a tube sheet manipulator arm 26 and associated guide tube 28, are connected to a conduit 32 which passes through a manway 34 in the steam generator plenum and is connected to a probe drive and take-up unit 36. The probe 24 is electrically energized through coaxial cables 38 enveloped within an outer sheath or wand that has a combination of rigidity and flexibility adapted for inserting the probe far up into the steam generator tubes and then pulling the probe through the tubes to generate electrical signals at a plurality of axial locations in each tube, commensurate with the tube inner diameter. These electrical signals are, as will be described more fully below, converted into digital form, stored, and processed, to determine the tube profiles and thus identify tube denting, bulging, or other potential problems. The probe cable 38 is electrically connected to a remote data acquisition unit 42, such as that available from the Zetec Corporation, Issaquah, Wash., as Model MIZ-18. The remote data acquisition unit is connected to a power source line 44, and transmits digitized data over a communications link 46 to an interface box 48, which is in turn connected to a computer 52, such as the Hewlett Packard Model HP9836 microcomputer. A data mass storage device, such as a 67 Mbyte data cartridge recorder 54, is also connected to the computer.

Preferably, the remote data acquisition unit 42, interface box 48, computer 52, and data recorder 54 are part of the MIZ-18 digital data acquisition system, as configured by Zetec and operated using the MIZ-18 data acquisition software available from Zetec.

It should thus be appreciated that the system for inspecting the internal profile of a substantially cylindrical field tube, includes a probe 24 having a cylindrical body and associated sensor coils, equipment 36 for drawing the probe through the tube, equipment 42 connected to the probe for energizing the coils and detecting electrical output signals from the probe at a plurality of axial locations in the tube, equipment 48, 54 for recording the values of the electrical signals as eddy current test values, and a computer 52 for converting the recorded values of ECT units to values radius at various axial locations in the tube to the user, i.e., through a screen display, printer, or some data storage media.

Figure 2:
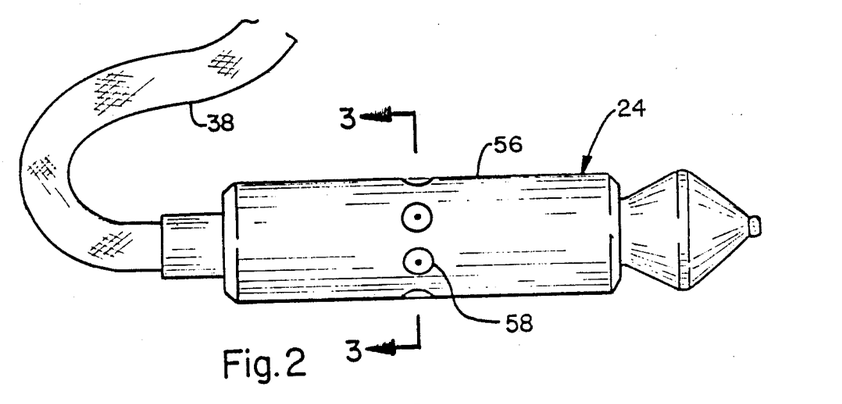
FIG. 2 is a side view of a typical eddy current probe and associated array of coils.
Figure 3:
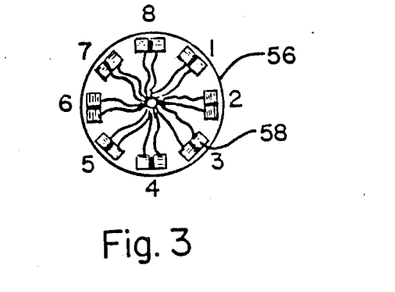
FIG. 3 is a section view of the probe of FIG. 2, taken along line 3—3.

FIGS. 2 and 3 show the details of a probe 24 for obtaining the eddy current profilometry data. The probe has a cylindrical body 56 portion, near the center of which are eight circumferentially spaced "pancake" coils 58. Each coil is individually energized and generates an ECT signal which is processed through the remote data acquisition unit 42 and stored in binary form in the cartridge recorder 54. For a typical steam generator tube having an OD of 0.75 inch and an ID of 0.654 inch, the OD of the probe body 56 would be 0.540 inch. The probe typically includes spacers (not shown) that maintain the probe centered on the tube axis if the tube is in fact cylindrical.

Figure 4:
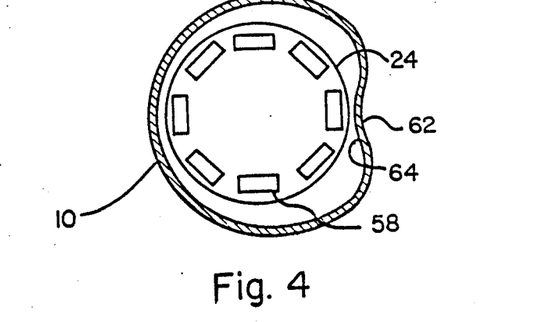
FIG. 4 is an enlarged section view through a tube having a deformed wall adjacent the inserted probe.

As shown in FIG. 4, even when the probe 24 passes through a region of the tube 10 containing a dent, 62 the spacer prevents the probe body from contacting the tube inner wall 64. It can be seen, however, that each coil 58 will experience a different eddy current effect because each coil in the dented region is likely to be a different distance from the adjacent portion of the tube wall 64.

It should be appreciated that the data analysis software used in conjunction with the MIZ-18 system 52 includes algorithms which display to the operator through the user interface, or record on the optional printer, the composite tube diameter along the line connecting any two diametrically opposed (oppositely disposed) coils, and the profile is inferred through a curve fitting algorithm wherein the eight measured radii are assessed and additional radii are predicted, resulting in a sufficient number of individual radii. This can be shown as at 66 on a screen, superimposed on the nominal tube inside diameter (see FIG. 1).

Figure 5:
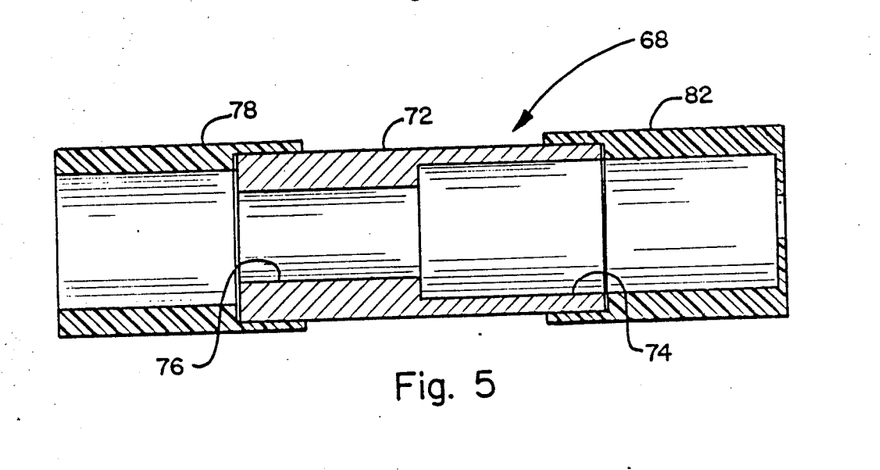
FIG. 5 is a side view of a calibration step tube having two regions of different circular cross section.

The mathematical algorithms used for converting data representing four diameters or eight radii, into the points representing the tube profile, depend for accuracy on the extent to which the digitized values of ECT stored in the cartridge recorder 54, can be calibrated to produce a predictable relationship between the ECT signal and the actual tube radius at which the ECT signal was generated. This calibration is conventionally achieved with this type of Zetec system, by the use of a calibration step tube standard 68, as shown in FIG. 5. The standard 68 has an active section 72 made of the same material as the field tube to be inspected, such as Inconnel 600. The standard has the field tube nominal outer diameter and, over approximately half the active section 72 as at 74, the field tube nominal inner diameter, i.e., 0.654 inch. Over the remaining portion of the active region at 76, a reduced step diameter of, e.g., 0.577 inches is provided. At either end of the active section 68, nylon end caps 78, 82 serve as probe centering guides, for the probe to be passed through first the nominal 74, and then the step 76 portions of the active section 72.

Conventionally, the operator records the ECT values generated in the nominal 74 and the step 76 portions of the standard 68, and, knowing the probe outer diameter, the operator (or, through software, the computer), consults a look-up table containing correction factors to be applied to the ECT data prior to generating the corresponding radii for use in the profilometry algorithms.

It has been known that the relationship between tube radius and ECT signals, for a given probe diameter, is nonlinear. This nonlinearity is accounted for, but only in a rough way, in the look-up correction tables associated with the prior art. ECT values which are not precisely equal to the values in the lookup table, must be interpolated, typically in software, and as a result suffer some degradation in accuracy.

The present invention is directed toward an improvement in the conversion of the recorded values of ECT to corresponding values of tube radius using the step tube standard of the type shown in FIG. 5, and the profilometry algorithms available with the Zetec system, or analysis software which users may wish to develop independently.

Figure 6:
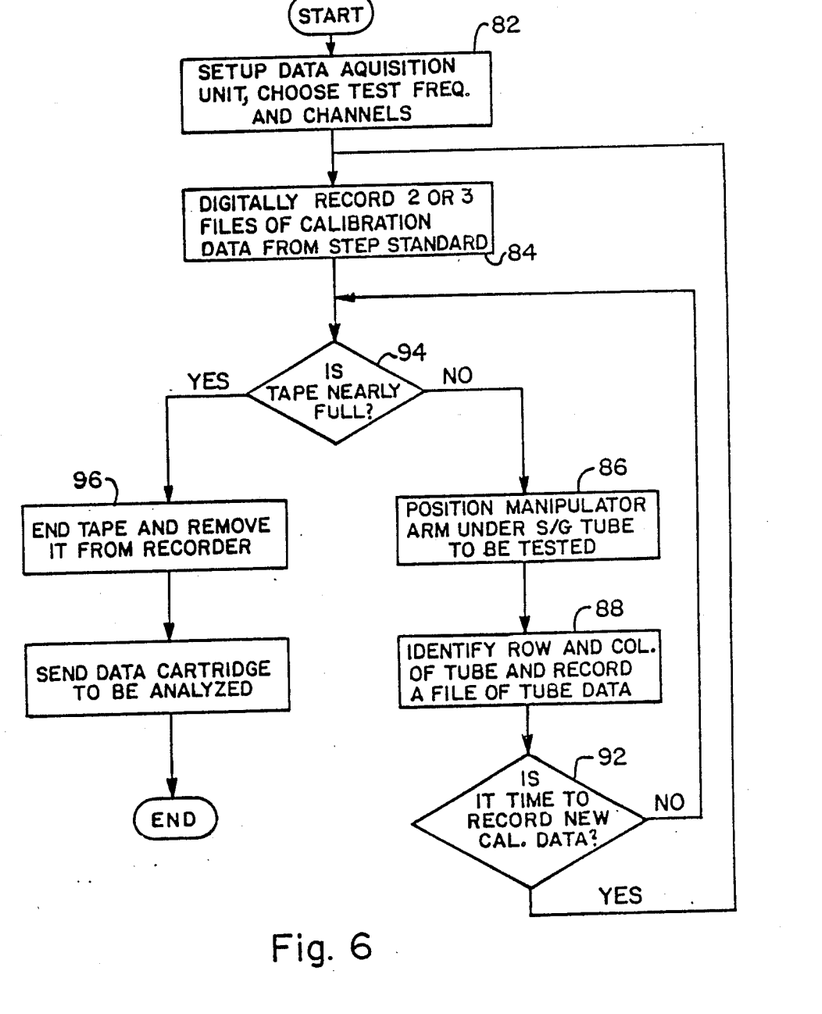
FIG. 6 is a flow chart illustrating the steps for acquiring both calibration and inspection data.

FIG. 6 is a flow chart showing the process for implementing the present invention. FIG. 6 should be used in conjunction with FIG. 1, as follows. The MIZ-18 system is set up at 82 in the conventional manner, with the operator choosing the frequencies and channels with which the data will be acquired. Once the data acquisition software has been loaded and the data acquisition subsystem 24, 36, 38, 42, 48, 54 is ready for operation, the probe 24 is passed through the step standard 68 shown in FIG. 5, preferably several times, to acquire and record in the storage device 54, ECT calibration values for each of the n, preferably eight, coils at the nominal and the step diameters of the standard 68. This calibration data is stored at the beginning of a data storage tape as indicated at 84. The probe 24 is then inserted fully into the field tube 10 to be inspected and the acquisition of field tube data begins as the probe is withdrawn through the tube Data are collected in discrete axial steps, typically every 0.050 inch. These data are in raw ECTU, and are archived in a separate file for each tube on the digital tape cartridge. As indicated at 86 and 88 the identity of each tube is obtained from position information on the manipulator arm 28 of the probe guide holding fixture 26 or, is manually entered into the computer. As indicated at 92 and 94, at intervals of approximately four hours, or when any system component or probe is changed, before the end of a data tape, and at the beginning and end of each shift, calibration data from the step standard is again acquired and stored. As each tape is completed as at 96, 98, the data cartridge is removed and analyzed. The analysis of the data on the tape cartridges can be made either at the trailer, using the HP9836 computer 52, or off-site, at a time different from the period during which data are being acquired.

It should be appreciated that the analysis of the data acquired for a particular tube will depend on the calibration data taken a short period before, after, or before and after the time at which the particular tube data were acquired. It should further be appreciated that since the relationship between ECT and tube radius is nonlinear, the acquisition of data from the step standard which has only two radii, does not uniquely define the nonlinear relationship. Moreover, this unique relationship must be established for each of the eight coils on the probe.

In accordance with the present invention, advantage is made of the insight that the diameter of the probe 24 can serve as a boundary condition on the nonlinear response of the probe to variations in the tube radius. With this additional information available for calibration, the nonlinear calibration curve can be inferred from two measurements, taken at two out of three known diameters.

Figure 7:
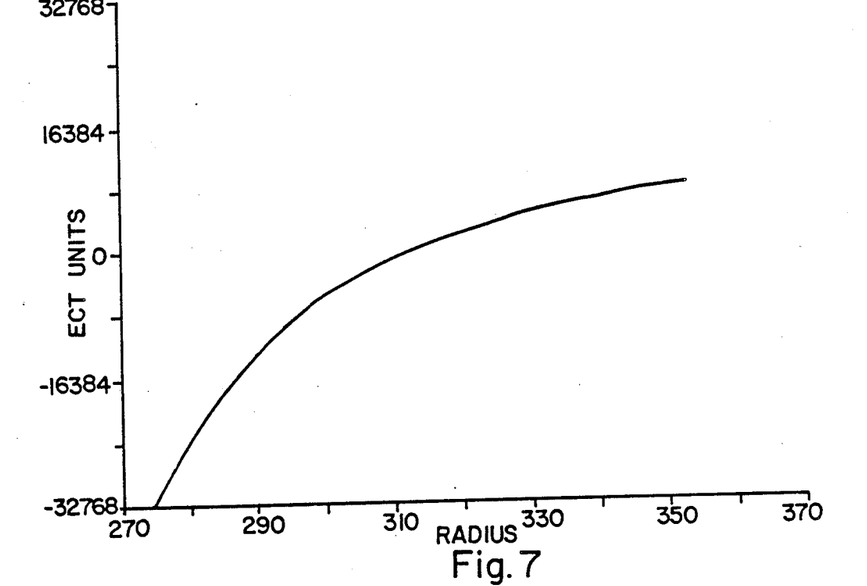
FIG. 7 is a graph showing a set of known circular tube radii and their corresponding ECT responses from a given probe.

In order to better understand the relationship between ECT signal output and tube radius, data were acquired from tube samples having a variety of radii, with a probe of uniform diameter. FIG. 7 illustrates a curve of the measured data points. From these data, it is postulated that the radius and ECT signals are related by a general relationship having the form, $$X = -1/Y. \quad \text{(Equation 1)}$$

In order to adjust the curve represented by this relationship to the data as shown in FIG. 7, the relationship is multiplied by a scaling constant, A, to give the relationship, $$X = -A/Y. \quad \text{(Equation 2)}$$

The curve defined by this relationship, now needs to be adjusted. To completely define the curve, values must be obtained for the axis intercepts, and/or the asymptotes. This requires solving for the constants A, B, and C, in the relationship $$X = -A/(Y+B) + C \quad \text{(Equation 3)}$$

where X is the tube radius
Y is the probe ECT signal
A is the scaling factor
B is the adjustment constant
C is the probe radius.

In accordance with the invention, the knowledge of the general shape of the relationship between ECT units and tube radius, as represented in FIG. 7 and Equation 1, is utilized to completely calibrate a probe using calibration measurements from a step tube standard such as shown in FIG. 5, to completely define the relationship appropriate to such standard, using Equation 3. This is accomplished by assuming that the probe cannot respond to diameters less than the probe diameter. Therefore the constant C in Equation 3 can define an asymptote of the curve of ECT units versus tube radius. This asymptote is a line corresponding to the probe radius. By applying this boundary condition, the constants A and B can be solved since, from the two step standard measurements, X and Y values are known at two conditions of Equation 3. Thus A and B can be determined from two equations in two unknowns.

It should be appreciated that this type of calibration is required for each of the n coils on the probe. Thus, each of the n coils will be assigned a first set of paired standard values of nominal tube radius and ECT, and a second set of paired standard values of the step radius and ECT, whereby calibration curves can be established for each probe. Each of the n coils will thus have associated with it n systems of equations, using the first and second sets of paired radii and ECT values, for determining the respective n values of A and B. Reference herein to sets of paired values does not require that the values be physically, paired side by side, in a computer 52 or mass data storage device 54, but only that such paired values be retrievable together for computing purposes.

Once the values of A, B, and C have been determined for each coil, the probe has been calibrated. Thereafter, in the data analysis subsystem 52, 54, 66, the ECT inspection value for any one of the n coils, taken from any axial location in the tube, can be selected from the data storage device 54 and a corresponding value of tube radius is obtained using the quantitative relationship of Equation 3. This value of radius is then communicated to the user through an interface device, which may be a screen display or a printer, or the data may be processed through an algorithm along with other such data, to produce a profilometry image 66, as is known in the art.

The method described immediately above, utilizing the relationship expressed in Equation 3, yields a curve with reasonable compliance to the available data such as shown in FIG. 7, but it is desirable that further accuracy be obtained. By tuning the constant C, this improvement in accuracy can be achieved. Physically, there are two reasons to further adjust the constant C. First, the probe coils 58 are typically recessed five to ten mils from the surface of the body 56 portion of the probe, to allow for a protective coating of epoxy. Secondly, if tube material were placed directly against the coil, it would not actually yield an infinite negative value for Y, the ECT signal. Some finite slope in response is expected since the coil and tube material have finite conductivity.

The constant C is adjusted with an offset that can be found empirically for a particular probe size. This is done iteratively by applying offsets in one mil increments and looking for the offset that yields the minimum error when comparing the curve to a known data set.

Since each of the n coils of a given probe size may have a different optimum offset, an average of the eight offsets is taken and this average offset becomes a parameter in the calibration algorithm for a given probe size. It is noted that adjustment of a few mils in the offset has minimal effect in the region of the step-to-nominal response. This is because of the nonlinear nature of the curve. A one mil adjustment in offset may result in approximately a 0.1 mil change in the step-to-nominal region. The offset corresponding to a given probe diameter can be stored in software in a look-up table.

Thus, in the preferred embodiment of the invention, each coil is calibrated in accordance with the relationship $$X_n = -A_n/(Y_n + B_n) + C - D. \quad \text{(Equation 4)}$$

where D is the look-up of the offset.

Figure 8:
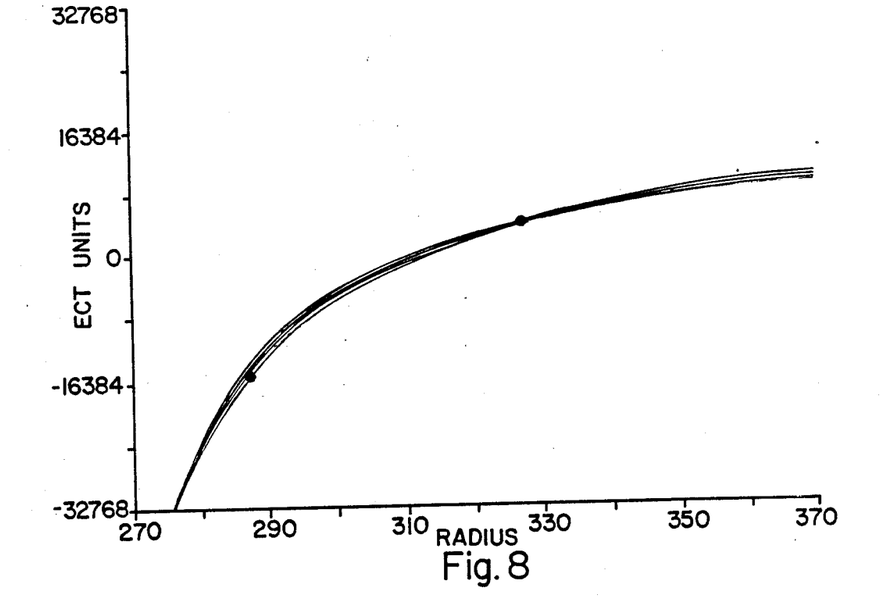
FIG. 8 is a graph of the eight separate calibration curves with their corresponding offsets applied, each superimposed over the set of responses for the known radii of FIG. 7.

FIG. 8 is a graph of the eight separate calibration curves with their respective optimum offsets applied. The eight curves are superimposed over the set of known points as shown in FIG. 7. When this calibration method is applied to field data collected with the same size probe, the average offset of seventeen will be applied to the calibration curves. The offsets corresponding to each of the coils represented in FIG. 8, are as follows:

| Coil Number | Offsets (ECTU) |
|---|---|
| 1 | 19 |
| 2 | 20 |
| 3 | 15 |
| 4 | 18 |
| 5 | 13 |
| 6 | 17 |
| 7 | 13 |
| 8 | 17 |

It can thus be appreciated that the apparatus and method in accordance with the present invention represents a simplification and improvement over the conventional technique of utilizing a lookup table for calibration of eddy current inspection probes. The present technique is easier to incorporate into the analysis subsystem of the type represented by MIZ-18 digital data analysis system, and provides more accuracy in the conversion of recorded values of eddy current signal response from a field tube, into radial measurements and thus indications of tube profilometry.

I claim:

1. A method of calibration an eddy current profilometry probe in a system for inspecting a substantially cylindrical field tube, the inspection system including a probe having a plurality n of sensor coils, a step tube standard having nominal and step diameters, a data acquisition subsystem connected to the probe, a data storage subsystem connected to the data acquisition system, and a data analysis subsystem including means for accessing the data in the storage subsystem and means for inferring from the accessed data, the radius of the tube at a plurality of axial locations in the tube, and a user interface for communicating the inferred radii to the user, wherein the method comprises the steps of:

passing the probe through the standard to acquire and record in the data acquisition subsystem and data storage subsystem, respectively, eddy current test (ECT) calibration values for each of the n coils at the nominal and the step diameters of the standard;

passing the probe through the tube to acquire and record in the data acquisition subsystem and the data storage subsystem respectively, ECT inspection values for each of the n coils at each of said axial tube locations;

with the data analysis subsystem, selecting from the data storage subsystem the ECT calibration values acquired from the nominal diameter portion of the standard with each of the n coils and assigning to each of the n coils a first set of paired values consisting of the nominal radius and the ECT calibration value from the nominal diameter portion of the standard;

with the data analysis subsystem, selecting from the data storage subsystem the ECT calibration values acquired from the step diameter portion of the standard with each of the n coils and assigning to each of the n coils a second set of paired values consisting of the step radius and the ECT calibration value from the step diameter portion of the standard;

forming n systems of equations, each system having two equations in two unknowns, each equation defining a quantitative relationship equivalent to $$X_i = -A_i/(Y_i + B_i) + C$$

where
$X_i$ is the tube radius
$Y_i$ is the probe ECT
$A_i$ is a scaling factor
$B_i$ is an adjacent constant
C is an adjacent constant radius
i is each of the 1 through n coils;

for each of the n system of equations, using said first and second sets of paired radii and ECT calibration values, for the quantities X and Y, respectively, to determine the values of A and B for each of the n coils;

selecting an ECT inspection value from the data storage subsystem for at least one of the n coils and determining a corresponding value of field tube radius using said quantitative relationship including said determined values of A and B for said selected coil; and communicating the determined value of the field tube radius to said user interface.

2. The method of claim 1, wherein the step of communicating includes communicating n determined values of field tube radius.

3. The method of claim 1, further including the step of generating a tube profile from the communicated values of field tube radius.

4. The method of claim 3, wherein the step of generating a tube profile includes generating a graphic image of the profile.

5. A system for inspecting the internal wall of a substantially cylindrical field tube, comprising:

a probe having a cylindrical body portion containing a plurality of circumferentially spaces sensor coils;

means for drawing the probe through a field tube with the coils spaced from the tube internal wall ;

means connected to the probe for energizing the coils and recording $Y_j$ values of eddy current test units (ECT) for respective $L_j$ axial locations in the tube; and means for converting the recorded values of ECT to values of tube radius and communicating the values of tube radius at each axial location in the tube to a user, the means for converting including, (a) means for storing a first radius value and a first ECT value generated by the probe when drawn through a cylindrical tube standard having a known first diameter, (b) means for storing a second radius value and a second ECT value generated by the probe when drawn through a cylindrical tube standard having a known second diameter, (c) means for storing a value commensurate with the radius of the probe body portion, (d) means for computing a quantitative relationship having the general form $$X_u = -A/(Y_u = B) + C$$

$$X_v = -A/(Y_v + B) + C$$

for the constants A and B, and storing the computed values of A and B wherein, $X_u$ is the stored first radius value $Y_u$ is the stored first ECT value $X_v$ is the stored second radius value $Y_v$ is the stored second ECT value C is the stored value of the radius of the probe body portion, (e) means for successively reading the stored values of A, B and C, and for successively reading each of the recorded values $Y_j$ of ECT for each axial location $L_j$ in the field tube, and (f) means for computing from the quantitative relationship $X_j = -A/(Y_j+B)+C$, the corresponding values $X_j$ of the tube radii at each location $L_j$ from each ECT value $Y_j$, respectively.

6. In a digital data processing system for reading a binary data file containing values of eddy current sensor output (ECT) associated respectively with values indicative of the sensor position within a tube to be inspected, the data processing system having means for converting the values of eddy current output to values of tube radius, and means connected to the means for converting, for communicating the profile of the tube through a user interface, the improvement which comprises:

means for storing a first radius value and a first ECT value generated by the probe when drawn through a cylindrical tube standard having a known first diameter;

means for storing a second radius value and a second ECT value generated by the probe when drawn through a cylindrical tube standard having a known second diameter;

means for storing a value commensurate with the radius of the probe body portion;

means for computing a quantitative relationship having the general form $$X_u = -A/(Y_u+B)+C$$

$$X_v = -A/(Y_v+B)+C$$

for the constants A and B, and storing the computed values of A and B, wherein $X_u$ is the stored first radius value $Y_u$ is the stored first ECT value $X_v$ is the stored second radius value $Y_v$ is the stored second ECT value C is the stored value of the radius of the probe body portion;

means for successively reading the stored values of A, B and C, and for successively reading each of the recorded values $Y_i$ of ECT for each axial location $L_i$ in the field tube; and means for computing from the quantitative relationship $X_i = -A/(Y_i+B)+C$, the corresponding values $X_i$ of the tube radii at each location $L_i$ from each ECT value $Y_i$, respectively.

* * * * *